(12) United States Patent
Slayton et al.

(10) Patent No.: US 7,950,522 B2
(45) Date of Patent: May 31, 2011

(54) CUSTOMIZABLE PACKAGE FOR FEMININE HYGIENE ARTICLES

(75) Inventors: Nancy Deters Slayton, Springfield, OH (US); Jeanne Marie Hughes, Loveland, OH (US); Virginia Anne Lenahan, Cincinnati, OH (US); David Andrew Dalton, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 78 days.

(21) Appl. No.: 12/414,875

(22) Filed: Mar. 31, 2009

(65) Prior Publication Data
US 2010/0244644 A1    Sep. 30, 2010

(51) Int. Cl.
*B65D 71/00*    (2006.01)
(52) U.S. Cl. ..... 206/229; 206/570; 206/440; 312/330.1; 312/259
(58) Field of Classification Search .................. 206/440, 206/733, 734, 555, 758, 388, 49, 229, 803, 206/570; 312/330.1, 290, 257.1, 327, 259
See application file for complete search history.

(56) References Cited

U.S. PATENT DOCUMENTS

| | | | | |
|---|---|---|---|---|
| 1,487,014 A * | 3/1924 | Davis | ............................ | 206/570 |
| 2,005,791 A * | 6/1935 | Kruse | ............................ | 312/209 |
| 4,261,627 A * | 4/1981 | Felsenthal | ..................... | 312/258 |
| 4,411,374 A * | 10/1983 | Hotchkiss | ....................... | 221/63 |
| 4,790,434 A * | 12/1988 | Schoberg et al. | ........ | 206/387.14 |
| 5,013,099 A * | 5/1991 | Styles et al. | .................. | 312/34.4 |
| 5,108,004 A * | 4/1992 | Baldwin | ........................ | 220/522 |
| 5,399,007 A * | 3/1995 | Marconet | ....................... | 312/209 |
| 5,558,229 A * | 9/1996 | Halbich | .......................... | 206/534 |
| 5,848,700 A * | 12/1998 | Horn | .............................. | 206/570 |
| 5,878,882 A * | 3/1999 | Kohagura | ..................... | 206/379 |
| 5,931,304 A * | 8/1999 | Hammond | ..................... | 206/570 |
| 5,992,630 A * | 11/1999 | Brown et al. | .................. | 206/497 |
| 6,164,442 A | 12/2000 | Stravitz | | |
| 6,688,466 B2 | 2/2004 | White et al. | | |
| 6,708,823 B2 | 3/2004 | Cottingham et al. | | |
| 7,147,129 B1 | 12/2006 | Minefield | | |
| 7,552,825 B2 * | 6/2009 | Caporrino | ..................... | 206/576 |
| 2002/0092792 A1 * | 7/2002 | Wolf, Jr. | ........................ | 206/579 |
| 2003/0071075 A1 * | 4/2003 | Frankenbach et al. | ..... | 222/383.1 |
| 2003/0136704 A1 * | 7/2003 | Burgess | ......................... | 206/581 |
| 2005/0029143 A1 * | 2/2005 | Samolinski et al. | .......... | 206/440 |

(Continued)

FOREIGN PATENT DOCUMENTS

EP    1 970 035 A1    9/2008

OTHER PUBLICATIONS

International Search Report & Written Opinion, PCT/US2010/028460, mailed Jun. 22, 2010, 13 pages.

*Primary Examiner* — David T Fidei
(74) *Attorney, Agent, or Firm* — Andrew J. Hagerty; Amanda T. Barry

(57) ABSTRACT

A package for feminine hygiene articles. The package includes a refillable cabinet having a front, a back, a top, a bottom, a first side, a second side, and a frame, the frame forming at least one feminine hygiene storage cavity having a frontward facing opening, and a plurality of replaceable drawers each containing a plurality of feminine hygiene articles and being slidingly installed within the feminine hygiene storage cavity.

8 Claims, 2 Drawing Sheets

U.S. PATENT DOCUMENTS

| | | |
|---|---|---|
| 2005/0137940 A1 | 6/2005 | Lindsay |
| 2005/0263575 A1 | 12/2005 | Weinmann |
| 2006/0266663 A1 | 11/2006 | Rhea |
| 2007/0032768 A1 | 2/2007 | Cohen et al. |
| 2007/0045144 A1 | 3/2007 | Wheeler et al. |
| 2007/0090014 A1 | 4/2007 | Wheeler et al. |
| 2007/0131577 A1* | 6/2007 | Call ............................ 206/570 |
| 2008/0111454 A1* | 5/2008 | Spoljaric ...................... 312/209 |
| 2009/0050503 A1 | 2/2009 | Snell |
| 2009/0115299 A1* | 5/2009 | Ricereto .................... 312/330.1 |

* cited by examiner

CUSTOMIZABLE PACKAGE FOR FEMININE HYGIENE ARTICLES

FIELD OF THE INVENTION

This invention relates to customizable packages, and more particularly, to customizable packages for one or more feminine hygiene articles.

BACKGROUND OF THE INVENTION

Feminine hygiene articles can include absorbent articles, such as, e.g. sanitary napkins, liners, tampons, interlabial products, and incontinence pads, as well as other articles such as, e.g., wipes or powder. There are many variations of sizes, shapes, and conformations of feminine hygiene articles, even within a particular category of feminine hygiene articles. As such, a user may use one type and/or size of feminine hygiene article throughout her menstrual cycle, or may use a combination of types and/or sizes during her menstrual cycle. For example, a user might use a regular size tampon throughout her entire menstrual cycle, perhaps in combination with a panty liner on certain days. Some users might use sanitary napkins on some days or overnight, and tampons on other days. Alternatively, a user might use different size products during her menstrual cycle, such as, e.g., a product with a higher absorbency on days of heavy flow and a product with a lower absorbency on lighter flow days.

Feminine hygiene articles are typically packaged by type and by size. For example, an ultra thin regular size sanitary napkin is generally packaged together with other ultra thin regular size sanitary napkins. Some feminine hygiene articles can be packaged together with other similar articles of different absorbencies, such as, e.g., in a multi-pack. In addition, feminine hygiene articles such as, e.g., sanitary napkins, can be packaged together with other articles such as, e.g., cleansing wipes. When a user wishes to use a combination of products, she generally must either conform to the product selections provided in a multi-pack package, or must purchase separate packages of the various products.

Packages of feminine hygiene articles are generally clearly labeled with the product information to allow for easier selection and purchase by a user. Once purchased, a user may desire to store the packages in a convenient location, such as, for example, near the toilet. Some users, however, may hide the packages in cabinets or other less convenient locations due to the personal nature of the packages.

As such, it would be desirable to provide a customizable package for feminine hygiene articles. It would also be desirable to provide a discreet package for feminine hygiene articles adapted for placement on a counter or other open space.

SUMMARY OF THE INVENTION

A package for feminine hygiene articles is provided. The package includes a refillable cabinet having a front, a back, a top, a bottom, a first side, a second side, and a frame, the frame forming at least one feminine hygiene storage cavity having a frontward facing opening, and a plurality of replaceable drawers each containing a plurality of feminine hygiene articles and being slidingly installed within the feminine hygiene storage cavity.

Also provided is a package for feminine hygiene articles including a refillable cabinet having a front, a back, a top, a bottom, a first side, a second side, and a frame, the frame forming at least one feminine hygiene storage cavity having a frontward facing opening, at least one wipes dispenser having a topward facing opening, a plurality of replaceable drawers containing a plurality of feminine hygiene articles and being slidingly installed within the feminine hygiene storage cavity, and a plurality of wipes installed within the wipes dispenser.

Also provided is a replaceable drawer pack for feminine hygiene articles. The pack includes a front, a back, a first side, a second side, a top, and a bottom, and is adapted to be installed in a feminine hygiene storage cavity of a refillable cabinet. The refillable cabinet can have a front, a back, a top, a bottom, a first side, a second side, and a frame, and the frame can form the feminine hygiene storage cavity that can have a frontward facing opening.

DETAILED DESCRIPTION OF THE INVENTION

Figure 1:
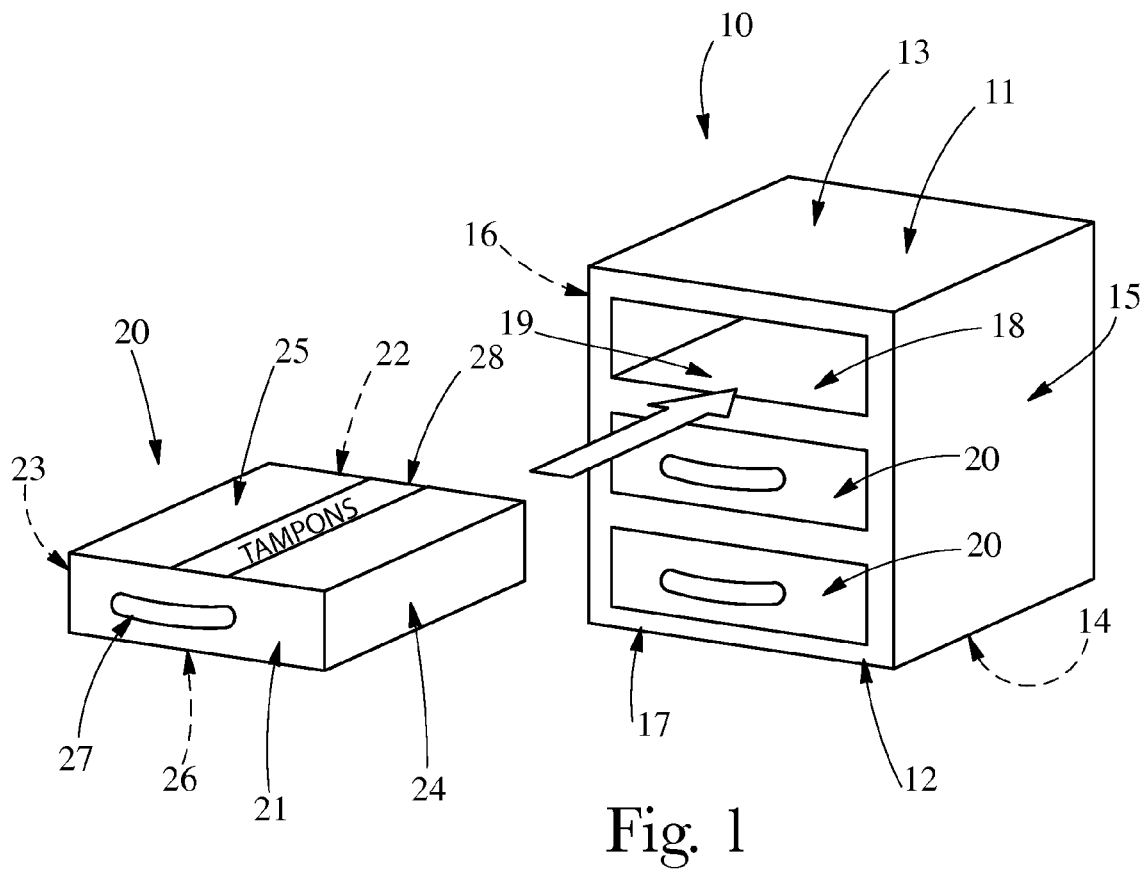
FIG. 1 is a perspective view of one embodiment of the invention.

The present invention relates to customizable packages. The customizable package can have a reusable cabinet and one or more replaceable drawers or other components that can be disposed within the cabinet. For example, such customizable packages can have a sturdy, attractive, and/or discreet reusable cabinet that can be filled with a plurality of packages that can be disposable and replaceable and that can contain a plurality of feminine hygiene articles. In certain embodiments, a consumer can purchase a reusable cabinet, that can be, for example, pre-filled with one or more retail packs of feminine hygiene articles that can, in certain embodiments, function as drawers when installed in the cabinet. Once the retail packs have been depleted, the user can refill the reusable cabinet with retail packs of her choice. In certain embodiments, the package can be a counter pack. The counter pack can be adapted for placement on a counter or other open surface and can be attractive and/or discreet. For example, in certain embodiments, the counter pack can be adapted to camouflage the feminine hygiene articles contained therein.

As used herein, the term "feminine hygiene article" refers to articles such as, e.g., disposable absorbent articles that can be worn by women for menstrual and/or light incontinence control, such as, for example, sanitary napkins, tampons, interlabial products, incontinence pads, and liners. As used herein, the term "feminine hygiene article" can also refer to other articles for use in the pudendal region such as, e.g. wipes and/or powder. As used herein, a feminine hygiene article can include any associated wrapping or applicator that typically can be associated with the feminine hygiene article. For example, a feminine hygiene article can be a tampon that may or may not include an applicator and/or can be a sanitary napkin that may or may not include a wrapper, such as, e.g., a wrapper that individually encloses the sanitary napkin.

As used herein, the term "absorbent article" refers to devices that absorb and/or contain a substance, such as, e.g., body exudates. A typical absorbent article can be placed against or in proximity to the body of the wearer to absorb and contain various body exudates.

As used herein, the term "tampon" refers to any type of absorbent structure such as, e.g., an absorbent mass, that can be inserted into the vaginal canal or other body cavity for the purpose of, such as, e.g. absorbing fluid therefrom, aiding in wound healing, and/or for delivering materials, such as moisture or active materials such as medicaments. The term "tampon" can also include the combination of an absorbent structure with any type of applicator that can be associated with the absorbent structure to facilitate insertion of a tampon into the vaginal canal or other body cavity. In certain embodiments, the term "tampon" can also include a wrapper that can individually package the tampon and/or the tampon in combination with an applicator.

As used herein, the term "retail pack" or "retail packages" refers to packages containing a plurality of feminine hygiene articles as sold in a retail environment. For example, feminine hygiene articles are typically packaged together in a bag or a box or other appropriate package for sale at a retail location. In certain embodiments, the feminine hygiene articles may be individually packaged prior to packaging in a retail pack or a vending machine; however, such individually packaged feminine hygiene articles themselves are not considered as a retail pack or retail package.

As used herein, the term "counter pack" refers to a package for feminine hygiene articles that is designed to be placed on a counter or other open surface. In certain embodiments, a counter pack can be adapted to contain a plurality of retail packs, and as such, will not be typically suitable for carrying in a purse due to size, configuration, or other characteristics.

FIG. 1 shows an example of a customizable package 10. The package 10 includes a refillable cabinet 11 that can have a front 12, a top 13, a bottom 14, a first side 15, and a second side 16. In certain embodiments, the refillable cabinet 11 can have a frame 17 that can form a plurality of feminine hygiene storage cavities 18. As shown in FIG. 1, each feminine hygiene storage cavity 18 can have a frontward facing opening 19. In certain embodiments, the package 10 can include a plurality of replaceable drawers 20 slidingly installed within feminine hygiene storage cavities 18. Each replaceable drawer 20 can include a plurality of feminine hygiene articles.

As shown in FIG. 1, each replaceable drawer 20 can have a front 21, a back 22, a first side 23, a second side 24, a top 25, and a bottom 26. In certain embodiments, the replaceable drawer 20 can include a handle 27 that can be used to pull the drawer 20 from the refillable cabinet 11. In addition, in certain embodiments, replaceable drawer 20 can be a retail pack. For example, as shown in FIG. 1, a surface of drawer 20, such as a surface that is not visible to a user when the drawer 20 is installed in cabinet 11, such as, e.g., top 25, bottom 26, back 22, first side 23, and/or second side 24, can include suitable retail pack information, such as, e.g., product brand, type, size, source identification, product codes, or other suitable information. In certain embodiments, surfaces of drawer 20 that are visible to a user when the drawer 20 is installed in cabinet 11, such as, e.g., front 21, can be provided to match and/or coordinate with cabinet 11, such as, e.g., in color, design, pattern, material, and/or in other suitable ways.

Figure 2:
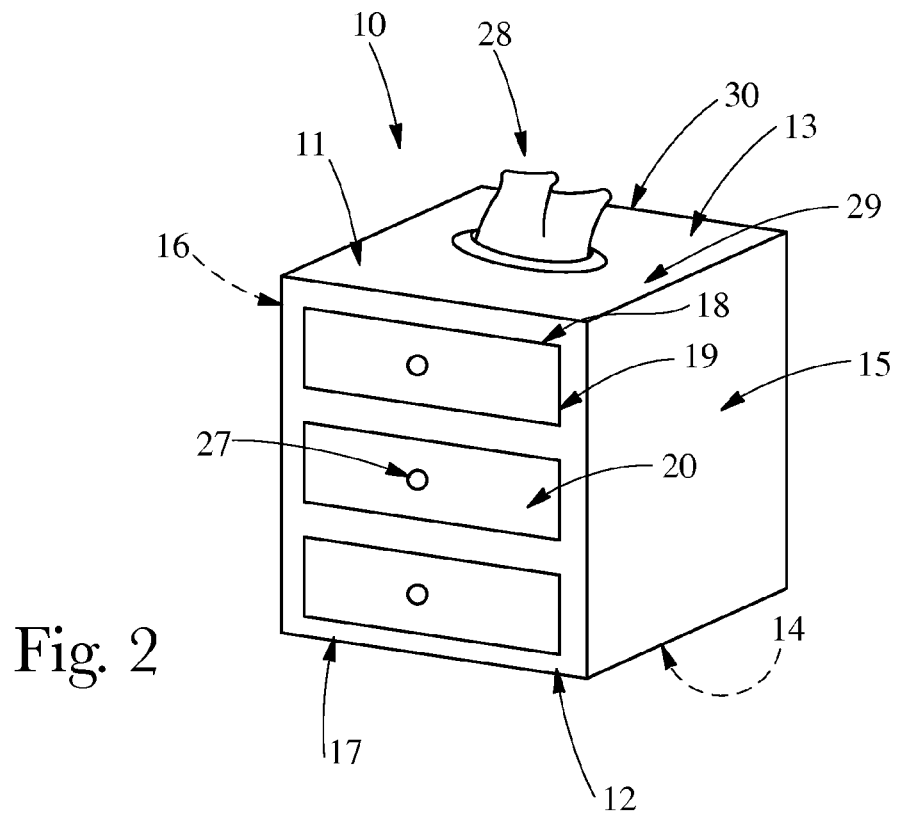
FIG. 2 is a perspective view of one embodiment of the invention.

FIG. 2 shows an example of a customizable package 10. The package 10 includes a refillable cabinet 11 that can have a front 12, a top 13, a bottom 14, a first side 15, and a second side 16. In certain embodiments, the refillable cabinet 11 can have a frame 17 that can form a plurality of feminine hygiene storage cavities 18. As shown in FIG. 2, each feminine hygiene storage cavity 18 can have a frontward facing opening 19. In certain embodiments, the package 10 can include a plurality of replaceable drawers 20 slidingly installed within the feminine hygiene storage cavities 18. Each replaceable drawer 20 can include a plurality of feminine hygiene articles. As shown in FIG. 2, cabinet 11 can be adapted to provide a wipes dispenser 28. In addition, cabinet 11 can include a lid 29 that can be removed or opened to provide access to wipes dispenser 28, such as, e.g., via hinge 30.

Figure 3:
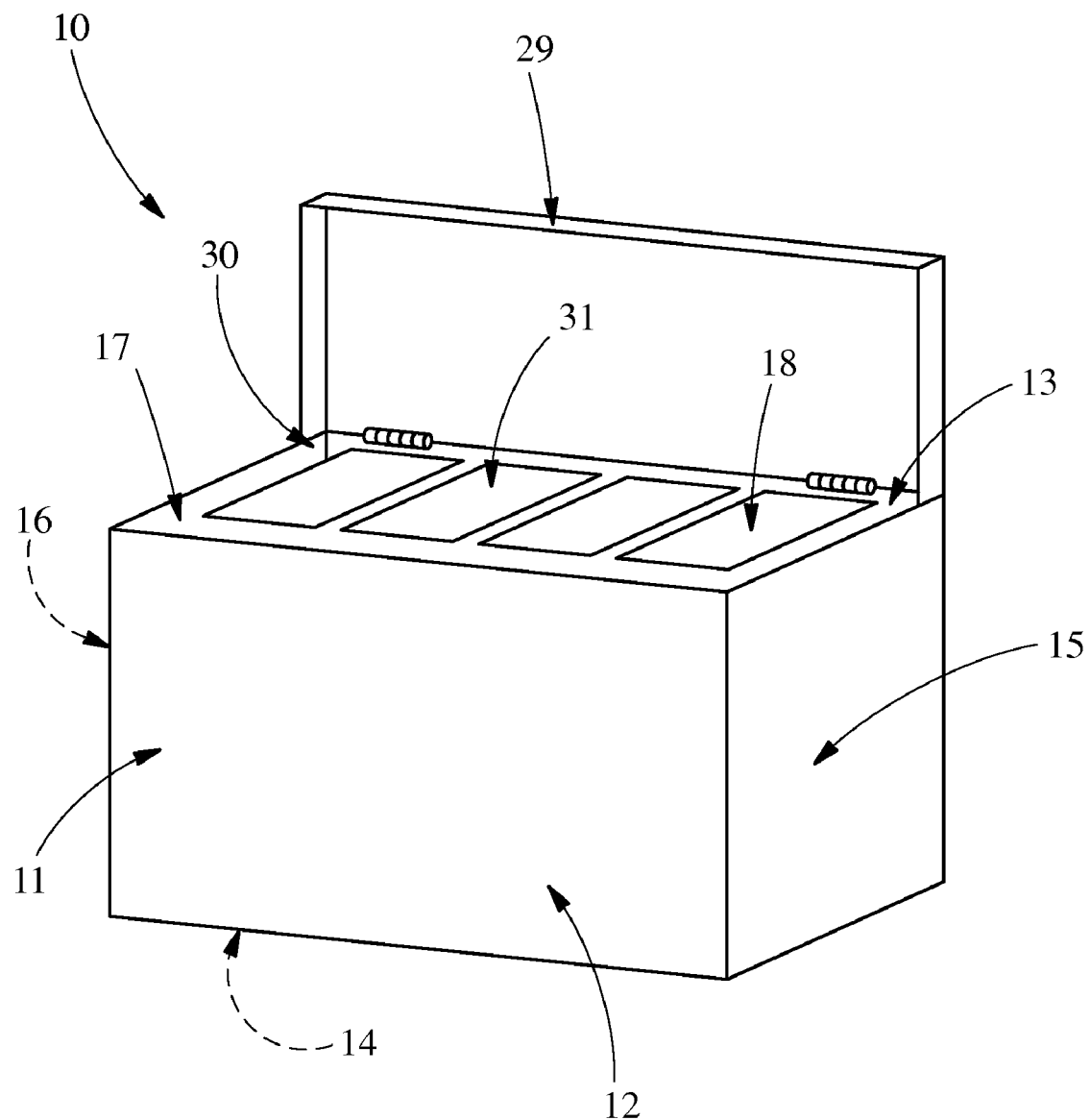
FIG. 3 is a perspective view of one embodiment of the invention.

FIG. 3 shows an example of a customizable package 10. The package 10 includes a refillable cabinet 11 that can have a front 12, a top 13, a bottom 14, a first side 15, and a second side 16. In certain embodiments, the refillable cabinet 11 can have a frame 17 that can form a plurality of feminine hygiene storage cavities 18. As shown in FIG. 3, each feminine hygiene storage cavity 18 can have a frontward facing opening 19. In certain embodiments, cabinet 11 can include a lid 29 that can be removed or opened to access feminine hygiene storage cavities 18, such as, e.g., via hinge 30. In addition, package 10 can include a plurality of replaceable drawers 20. Alternatively, package 10 can include a plurality of retail packs 31 that can fit into feminine hygiene storage cavities 18. In certain embodiments, lid 29 can be adapted to cover feminine hygiene storage cavities 18 and retail packs 31 disposed therein.

The refillable cabinet can have any suitable design. In certain embodiments, the refillable cabinet can be formed from a sturdy material such that the cabinet can be reused and may not need to be repurchased frequently. For example, in certain embodiments, the refillable cabinet can be constructed of plastic or other inflexible and/or reinforced materials. In addition, the cabinet can be adapted to contain any suitable number of retail packs and/or replaceable drawers, such as, e.g., one retail pack or replaceable drawer, a plurality of packs and/or drawers, such as, e.g., two or more, three or more, four or more, five or more, or any other suitable number and combination of retail packs and/or replaceable drawers.

In certain embodiments, the cabinet can include a number of feminine hygiene storage cavities that corresponds to the number of retail packs and/or replaceable drawers that can be disposed within the cabinet. Alternatively, the cabinet can include one or more feminine hygiene storage cavities that can contain a plurality of retail packs and/or replaceable drawers within a single cavity. In certain embodiments, the feminine hygiene storage cavity can be configured to hold a specific size, such as, e.g., a specific type or brand, or retail pack or replaceable drawer. Alternatively, the feminine hygiene storage cavity can be configured to hold a variety of types or brands of retail packs or replaceable drawers, such as, e.g., by including an adapter or other device.

The feminine hygiene storage cavities can include a frontward facing opening. As set forth herein, the side of the package including the feminine hygiene storage cavity openings can be considered as the "front" of the package. In certain embodiments, a user may store or display the customizable package with the openings parallel to the counter or other surface and/or may store or display the package with the openings perpendicular to the counter or other surface; however, the side of the package including the openings can still be considered the front of the package as described herein.

While the refillable cabinet can be suitable for multiple uses, the retail packs and/or replaceable drawers can be disposable. In certain embodiments, the retail packs and/or replaceable drawers can be conventionally marketed retail packs. In addition, in certain embodiments, the retail packs or replaceable drawers can include additional features, such as, e.g., a design or configuration on the surface that can correspond to the visible face when the pack or drawer is loaded into the cabinet, and/or an opening device provided on the surface of the pack or drawer that will be accessible when the pack or drawer is loaded into the cabinet, and/or, in the case of a replaceable drawer, a handle, such as, e.g., a handle or pull. In certain embodiments, the replaceable drawer or retail pack can have an opening that can be configured to provide a tilt out bin for accessing the feminine hygiene articles contained therein.

The refillable cabinet can be loaded with replaceable drawers and/or retail packs. In certain embodiments, the replaceable drawers can be retail packs that can have, for example, additional features. For example, in certain embodiments, replaceable drawers can function as a retail package, such as, e.g., by including typical retail package information, with the addition of a surface that is decorative and/or lacking in prominent feminine hygiene article information. In addition, in certain embodiments, a replaceable drawer can include a handle, pull, or other suitable device, that can be part of the replaceable drawer when purchased or that can be provided in the package and attached after purchase but prior to loading the drawer into the cabinet. In certain embodiments, the replaceable drawers can be configured to attach together, such as, e.g., to form a storage unit and/or cabinet.

The retail packs, replaceable drawers, and corresponding feminine hygiene storage cavities can be any suitable size. In certain embodiments, the packs, drawers, and storage cavities can correspond to the size of currently marketed feminine hygiene article packaging. For example, in certain embodiments, the retail packs and replaceable drawers can be about 3 to about 6 inches wide, such as, e.g., about 4 to about 5 inches wide, about 4 to about 7 inches high, such as, e.g., about 5 to about 6 inches high, and about 1 to about 3 inches deep, such as, e.g., about 2 inches deep, or any other suitable size, such as, e.g., a size suitable to containing a pack for wipes, powder, compact tampons, digital tampons, liners, sanitary napkins, tampons, or any other suitable size, and the storage cavities can be suitable to contain retail packs and/or replaceable drawers of that size. Alternatively, in certain embodiments, the packs, drawers, and storage cavities can be a custom size, such as, e.g., a size corresponding to the customizable package configuration.

The package can be made of any suitable material. In certain embodiments, the package can comprise one or more inflexible materials, such as, for example, cardboard, paperboard, cartonboard, chipboard, plywood, SBS, metal, plastic, paper, card stock, fabric, ceramic, polymer, natural or synthetic fibers, webs, mesh, screen, wood, composite, mixtures or combinations thereof, or any other suitable material.

Any suitable feminine hygiene article and/or combination of feminine hygiene articles can be disposed in the package. Suitable feminine hygiene articles include, e.g., absorbent articles, such as, e.g., tampons, sanitary napkins, pantiliners, incontinence articles, and/or interlabial pads, and other articles such as, e.g., wipes and/or powder.

In certain embodiments, the customizable package can have additional features. For example, in certain embodiments, the refillable cabinet can include a disposal bag feature, an air freshener dispenser, a child proof lock, antibacterial hand products, lotions, or any other suitable features.

To use the customizable package, a consumer can purchase the reusable cabinet, that can, in certain embodiments, be pre-filled with one or more retail packages and/or replaceable drawers. The user can leave the cabinet in a convenient location, such as, e.g., on a bathroom counter or on the back of the toilet. When the user wishes to use a feminine hygiene article, she can select and open the appropriate drawer or pack and remove the article for use. Once a particular drawer or pack is empty, she can remove the drawer or pack from the feminine hygiene article opening and refill the space with a new drawer or pack of her choice. As such, the user is able to customize the package to her liking. In addition, in certain embodiments, the package can be attractive and/or discreet such that it can be stored in a convenient location.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A package for feminine hygiene articles, the package comprising:
    a refillable cabinet comprising a front, a back, a top, a bottom, a first side, a second side, and a frame, the frame forming at least one feminine hygiene storage cavity having a frontward facing opening and at least one wipes dispenser having a topward facing opening;
    a plurality of replaceable drawers each containing a plurality of feminine hygiene articles and being slidingly installed within the feminine hygiene storage cavity, and each including a handle adapted to pull the replaceable drawer outwardly from the feminine hygiene storage cavity;
    a plurality of wipes installed within the wipes dispenser.

2. The package of claim 1, wherein the replaceable drawer includes a front, a back, a first side, a second side, a top, a bottom, and wherein the replaceable drawer includes a frontward facing surface that aligns with the frame, the frontward facing surface being configured to coordinate with the refillable cabinet.

3. The package of claim 1, wherein the package is a counter pack.

4. The package of claim 1, wherein the number of feminine hygiene storage cavities corresponds to the number of replaceable drawers.

5. The package of claim 1, wherein the replaceable drawers are adapted to function as retail packs.

6. The package of claim 1, wherein the replaceable drawers are from about 3 to about 6 inches wide, about 4 to about 7 inches high, and about 1 to about 3 inches deep.

7. The package of claim 1, wherein the refillable cabinet is formed from plastic.

8. The package of claim 1, wherein the refillable cabinet is formed from cardboard, paperboard, cartonboard, or combinations thereof.

* * * * *